(12) United States Patent
Manczinger et al.

(10) Patent No.: US 9,538,764 B2
(45) Date of Patent: Jan. 10, 2017

(54) **ACTIVE AGENTS AGAINST *PSEUDOMONAS* SPECIES CAUSING ROTTING DISEASES IN MUSHROOM PRODUCTION, THEIR USE AND COMPOSITIONS CONTAINING THEM**

(75) Inventors: László Manczinger, Szeged (HU); Csaba Vágvölgyi, Szőreg (HU); Enikö Sajben, Szeged (HU); Árpád Nagy, Szeged (HU); Zoltán Szöke-Kis, Mezöberény (HU); Adrienn Nagy, Kecskemét (HU); György Turóczi, Gödöllö (HU); András Kovács, Kecskemét (HU)

(73) Assignee: Szegedi Tudományegyetem, Szeged (HU)

( * ) Notice: Subject to any disclaimer, the term of this patent is extended or adjusted under 35 U.S.C. 154(b) by 116 days.

(21) Appl. No.: 14/343,268

(22) PCT Filed: Aug. 30, 2012

(86) PCT No.: PCT/HU2012/000085
§ 371 (c)(1),
(2), (4) Date: May 27, 2014

(87) PCT Pub. No.: WO2013/034939
PCT Pub. Date: Mar. 14, 2013

(65) Prior Publication Data
US 2014/0377239 A1     Dec. 25, 2014

(30) Foreign Application Priority Data

Sep. 8, 2011 (HU) ..................... 1100496

(51) Int. Cl.
*A01N 63/00* (2006.01)
*C12R 1/38* (2006.01)
*C12N 1/20* (2006.01)

(52) U.S. Cl.
CPC .............. *A01N 63/00* (2013.01); *C12N 1/20* (2013.01); *C12R 1/38* (2013.01)

(58) Field of Classification Search
CPC .............. A01N 63/00; C12N 1/20; C12R 1/38
See application file for complete search history.

(56) References Cited

U.S. PATENT DOCUMENTS

2009/0214502 A1* 8/2009 Gheshlaghi ............ A01N 63/00
424/93.462

FOREIGN PATENT DOCUMENTS

| | | |
|---|---|---|
| EP | 0 210 734 A1 | 2/1987 |
| JP | 2008-11830 A | 1/2008 |
| KR | 2004-0078027 A | 9/2004 |

OTHER PUBLICATIONS

Fermor et al.: "Bacterial blotch disease of the cultivated mushroom *Agaricus bisporus*: screening, isolation and characterization of bacteria antagonistic to the pathogen (Pseudomonas tolaasii)", Journal of Applied Bacteriology, 1988, vol. 65, pp. 179-187.
Sajben et al.: "Characterization of pseudomonads isolated from decaying sporocarps of oyster mushroom", Microbiological Research, May 2011, vol. 166, pp. 255-267.
Elbanna et al.: "Characterization of Egyptian Fluorescent Rhizosphere Pseudomonad Isolates with High Nematicidal Activity against the Plant Parasitic Nematode Meloidogyne Incognita", J Biofertil Biopestici, 2010, vol. 1, No. 1, pp. 1-7.
Fang et al.: "A broad-spectrum antagonistic activity of the biocontrol agent Pseudomonas synxantha BG33R", Phytopathology, 2007, vol. 97, abstract.
Anzai et al.: "Phylogenetic affiliation of the pseudomonads based on 16S rRNA sequence", Inernational Journal of Systematic and Evolutionary Mocrobiology, 2000, vol. 50, pp. 1563-1589.
Sajben-Nagy: "Investigation of pseudomonads, pathogenic to oyster mushroom and the possibilities of their biological control", University of Szeged Faculty of Science and Informatics Department of Microbiology, Oct. 2011, pp. 1-10.
Sahin: "Antimicrobial activity of *Streptomyces* species against mushroom blotch disease pathogen", J. Basic Microbiol., 2005, vol. 45, pp. 64-71.

* cited by examiner

Primary Examiner — Susan Hanley
(74) Attorney, Agent, or Firm — Jason D. Voight

(57) ABSTRACT

A biological material is disclosed for exerting antagonism against the mushroom pathogen *Pseudomonas* bacteria, which contains the *Pseudomonas synxantha* PS54 bacterium strain deposited under # NCAIM (P) B 001387 according to the Budapest treaty. The biological material according to the invention is an effective antagonist against the pathogens of mushrooms, in particular oyster mushrooms and/or champignons, in particular *Pseudomonas tolaasii* and *Pseudomonas agarici*. Furthermore, the invention relates to a composition comprising a culture of the biological material according to the invention, the use of the invention for the protection of mushrooms, and a process for controlling pathogens. The invention further relates to an agent for producing mushrooms, which agent has been contacted with the biological material according to the invention.

5 Claims, 2 Drawing Sheets

SEQUENCE LISTING

<160> NUMBER OF SEQ ID NOS: 5

<210> SEQ ID NO 1
<211> LENGTH: 22
<212> TYPE: DNA
<213> ORGANISM: Artificial Sequence
<220> FEATURE:
<223> OTHER INFORMATION: primer to amplify a region of rpoB

<400> SEQUENCE: 1
tggccgagaa ccagttccgc gt                                        22

<210> SEQ ID NO 2
<211> LENGTH: 22
<212> TYPE: DNA
<213> ORGANISM: Artificial Sequence
<220> FEATURE:
<223> OTHER INFORMATION: primer to amplify a region of rpoB

<400> SEQUENCE: 2
cggcttcgtc cagcttgttc ag                                        22

<210> SEQ ID NO 3
<211> LENGTH: 21
<212> TYPE: DNA
<213> ORGANISM: Artificial Sequence

```
<220> FEATURE:
<223> OTHER INFORMATION: primer to sequence a section of the rpoB gene

<400> SEQUENCE: 3
agttcatgga ccagaacaac c                                              21

<210> SEQ ID NO 4
<211> LENGTH: 20
<212> TYPE: DNA
<213> ORGANISM: Artificial Sequence
<220> FEATURE:
<223> OTHER INFORMATION: primer to sequcence a section of the rpoB gene

<400> SEQUENCE: 4
ccttgacggt gaactcgttc                                                20

<210> SEQ ID NO 5
<211> LENGTH: 20
<212> TYPE: DNA
<213> ORGANISM: Artificial Sequence
<220> FEATURE:
<223> OTHER INFORMATION: primer to sequcence a section of the rpoB gene

<400> SEQUENCE: 5
ccttcacggt gaattcgttc                                                20
```

ACTIVE AGENTS AGAINST *PSEUDOMONAS* SPECIES CAUSING ROTTING DISEASES IN MUSHROOM PRODUCTION, THEIR USE AND COMPOSITIONS CONTAINING THEM

This is the national stage of International Application PCT/HU2012/000085, filed Aug. 30, 2012.

BRIEF DESCRIPTION OF THE INVENTION

The invention relates to a biological material for exerting antagonism against fungi pathogenic *Pseudomonas* bacteria, which contains *Pseudomonas synxantha* PS54 bacterium strain deposited under # NCAIM (P) B 001387 on Aug. 8, 2011 at the National Collection of Agricultural and Industrial Microorganisms, Somlói út 14-16, 1118 Budapest, Hungary, according to the Budapest Treaty. The biological material according to the invention is an effective antagonist against the pathogens of cultivated mushrooms, primarily oyster mushrooms and/or champignon, in particular against the pathogens selected from the group of *Pseudomonas tolaasii, Pseudomonas agarici*. Furthermore, the invention relates to a composition comprising a culture of the biological material according to the invention, use of the composition for the protection of cultivated mushroom, and a process for controlling pathogens. The invention also relates to a composition for the growth of cultivated mushrooms that were treated with the biological material according to the invention.

BACKGROUND OF THE INVENTION

Nowadays there is an increasing need in the fields of vegetable and mushroom production and sales for bioproducts containing no residues of chemical pesticides. Among the effective chemical pesticides only the inorganic copper-compositions are allowed in the course of production of bioproducts. The number of copper resistant mutants among the vegetable pathogen microorganisms has increased a lot in the last couple of years, thus these copper containing agents alone are insufficient to achieve effective and reliable pest control. One possible solution to overcome this problem is to effect an integrated pest control using copper containing agents and biocontrol compositions. Biocontrol products may also be used alone, but in such cases the highest efficiency of the best compositions is still under 50 percent. The majority of the antibacterial or antifungal biocontrol products presently available in the world market contain one component as active agent, which is a bacterium or fungi possessing antagonist and/or parasite features.

The bacterial maculation may affect every produced mushroom species in the field of mushroom production, strains less susceptible (or even resistant) to the pathogen are not known to date. The bacterial maculation infects very quickly in the mushroom production premises because on one hand the *Pseudomonas* strains are very aggressive pathogens through their toxins and on the other hand the conditions of the mushroom production are ideal for them. The loss of the yield often reaches even 50 to 60 percent. The damage caused by this bacterial pathogen represents as much as 800 million HUF loss in revenues per annum considering an average of 25 000 tons of the cultivated mushroom per year. The situation is made even worse by the fact that there is no registered pest controlling agent in the mushroom production.

Certain strains of the *Pseudomonas* genus, among them especially *Pseudomonas fluorescens* strains have long been used for biocontrol purposes. There are marketed compositions which are effective mainly against plant pathogen fungi. Their effectiveness is first of all explained by different antibiotics secreted to the extra-cellular space, which antagonize mainly fungi: phenazine derivatives, 2,4-diacetylfloroglucinol, and pyrrolnitrin. *Pseudomonas fluorescens* strains are also successfully used against bacteria for biocontrol. E.g. a *Pseudomonas* species producing 2,4-diacetylfloroglucinol (DAPG) was used against *Erwinia* causing bacterial soft rot in potato. In the presence of the DAPG producing *Pseudomonas* the plant was not infected. The results show that DAPG is a significant biocontrol against determinant bacteria as well. The antibiotics secreted by bacteria are capable of inhibiting the life functions of other microorganisms already at low concentration, and even causing their death. In cases of a number of plants it is proven that the antibiotics production of the bacteria suppressed the plant pathogen and the disease caused by it. It has been demonstrated that these effects are present not only in laboratory circumstances, but also in a natural environment, in the soil. To perform an effective biocontrol, the species used must produce sufficient amount of the antibiotics in the proximity of the pathogen. The particular amount needed is highly varied and is different in cases of the different pathogens. In case of a number of *Pseudomonas* strains used in biocontrol the multiplied antibiotics production is known. The effectiveness of *P. fluorescens* is further increased by the excellent competition capability of the strains. In the competition among the *Pseudomonas fluorescens* strains the competition with siderophores (iron-binding organic compounds) for the free iron-ions has high importance as well. The biocontrol based on competition has successfully been used against e.g. *Agrobacterium radiobacter, A. tumefaciens*, or the pathogen *Fusarium oxysporum, F. oxysporum* strains.

THE STATE OF THE ART

Parret et al. (Appl Environ Microbiol. 2005 September; 71(9):5197-207) investigated the activity of bakteriocin (antibacterial protein) llpA1(Pf-5) or llpA2(Pf-5) produced by *Pseudomonas fluorescens* Pf-5 strain. The authors found that the tested antibacterial proteins are capable of inhibiting *Pseudomonas fluorescens* and other *Pseudomonas* strains. Furthermore, it can be seen from the published test data that the *Pseudomonas fluorescens* Pf-5 strain inhibits the mushroom pathogen bacterium *Pseudomonas agarici* as well.

The objective of Bora and Özaktan (Proceedings of the 15th International Congress on the Science and Cultivation of Edible Fungi, Maastricht, Netherlands, 15-19 May, 2000. 2000 pp. 689-693) was to identify antagonist fluorescent *Pseudomonas* strains that may effectively be used against different pathogens, such as a *Papulaspora byssina, Cladobotryum dendroides, Pseudomonas tolaasii* és *Mycogone perniciosa*. According to the results the *Pseudomonas fluorescens* M 4/2, *Pseudomonas fluorescens* M 5/3 and *Pseudomonas putida* 39 strains were capable of significantly decrease the severity of the disease caused by *Pseudomonas tolaasii*.

Sahin et al. (J Basic Microbiol. 2005; 45(1):64-71) isolated and identified three *Streptomyces* species that demonstrated antimicrobial activity against *Pseudomonas tolaasii* NCPPB 2192(T). Six strains showed high activity, which were classified by the authors as follows: *Streptomyces rochei, Streptomyces lydicus* and *Streptomyces antibioticus*. The authors demonstrated that the biologically active compounds are likely to contain a beta-lactame ring.

EP0210734 relates to antagonist *Pseudomonas fluorescens* strains useful in the biocontrol against *Pseudomonas tolaasii* causing the disease of cultivated fungi, which strains were deposited under NCIB 12087, NCIB 12088, NCIB 12089 or NCIB 12090. The isolated *Pseudomonas fluorescens* strains are rifampicin resistant. The effectiveness of the *Pseodumonas fluorescens* isolated according to the patent application is the most suitable when used in combination, and at least two applications are necessary for the prophylaxis of the maculation of the fungus.

JP2008011830 Japanese patent publication document relates to the control of bacteria belonging to the *Pseudomonas* genus, to promote the growth of cultivated mushrooms. The method suggests the use of positively and negatively charged ions for the given purpose. The method may be used even in a high humidity environment to control bacteria. The method disclosed in said patent application is not a biological control of pathogens.

KR20040078027 Korean patent publication document relates to a *Pseudomonas putida* CI-9(KCTC 10075BP) strain isolated from the surface of the mycelia of the mushroom, which promotes the growth and development of cultivated mushrooms. Furthermore, the patent application relates to a method for the production of mushroom using said bacterium strain. The bacterium strain disclosed in the prior art reference is capable of inhibiting the mushroom disease caused by *Pseudomonas tolaasii* in cases of both oyster mushroom and saffron milk cap (*Lactarius deliciosus*).

From the above it can be seen that although there are different methods according to the state of the art that may solve the problem of controlling the pathogens of cultivated mushrooms, especially *Pseudomonas tolaasii* and *Pseudomonas agarici*, however, the majority of the methods targets only the protection against *Pseudomonas tolaasii* among the most important pathogens of the cultivated mushrooms, and not against *Pseudomonas agarici*, furthermore, their effectiveness is not in all cases acceptable. Therefore, there is high demand for economical and effective compositions performing biological control of pathogens, which are especially useful to effectively combat detrimental microorganisms attacking cultivated mushrooms. There is a need therefore for novel compositions, which would overcome the drawback of the state of the art, especially the application of complicated, multiple step and environmentally stressing pest control technologies. In order to meet these needs we have done systematic research and development, as a result of which we have completed our invention.

DETAILED DESCRIPTION OF OUR INVENTION

Definitions

The term "*Pseudomonas synxantha*" as used in the present description means the strains of the bacterium species *Pseudomonas synxantha* belonging to the genus *Pseudomonas*; the strain applicable in the present invention is the *Pseudomonas synxantha* PS54 strain deposited under deposit No. NCAIM (P) B 001387 according to the Budapest Treaty.

The term "pest" or "pathogen" as used in the present description means a virus, bacterium or fungus, which lives parasitically in different living organisms, and settling and reproducing in the host or its body (e.g. in a human) causes a disease. The measure of the ability to infect, the pathogenity, may be variable even within one species.

The term "antagonist effect" or "antagonism" as used in the present description means a relationship between microorganisms, in which the members of one species are killed, deterred, or their reproduction is inhibited by the representatives of another species, e.g. through the chemicals (e.g. antibiotics, extracellular enzymes) produced by them.

The term "excipient" as used in the present description is not particularly limited, and the excipients may be selected from the group as follows:
a) in case of a liquid formulation e.g. water or an organic solvent (e.g. xilene, methanol, ethylene-glycol or mineral oil), a dispersion stabilizator, a surfactant (e.g. calcium-dodecyl-benzene-sulphonate, polyglycol-ether, etoxylated alkyl-phenol or alkyl-aryl-sulphonates), optionally waxes,
b) in case of a granular formulation montmorillonite, bentonite, wood flour, starch, cellulose and a binder, such as e.g. a mineral oil, polyvinyl-alcohol or saccharose,
c) and other in itself known, usual additive and/or excipient.

The excipient according to the invention may be selected by the skilled person without undue experimentation.

The term "dose formulation" as used in the present description characterises the type of formulation according to the composition, which is determined according to the *Pesticide formulation types and international coding system catalogue* (Crop-Life International Technical Monography, No. 2; $5^{th}$ Edition, 2002). This may be e.g. aqueous suspension, suspension concentrate, capsulated concentrate, emulsion forming liquid spray, granule, granule dispersible in water, microgranule, water soluble powder, but is not limited thereto. The dose formulation which may be used according to the invention may be selected by the skilled person without undue experimentation.

The Discovery According to the Invention

As a result of the systematic experimental work directed to the present invention we have surprisingly found that the *Pseudomonas synxantha* PS54 bacterium strain tested by us exerts a stronger antagonist activity as compared to the state of the art against pathogens, and thank to this effect, the extent of the infections caused by *Pseudomonas* was significantly decreased in case of cultivated mushroom.

DETAILED DESCRIPTION OF THE INVENTION

Based on the above, the present invention relates in its first aspect to a biological material for exerting antagonism against pathogen *Pseudomonas* bacteria, which contains *Pseudomonas synxantha* PS54 bacterium strain deposited under # NCAIM (P) B 001387 according to the Budapest Treaty. The biological material according to the invention is an effective antagonist against the pathogens of cultivated mushrooms, preferably oyster mushrooms and/or champignons, in particular against the following pathogens: *Pseudomonas tolaasii, Pseudomonas agarici*.

Accordingly, the *Pseudomonas synxantha* strain that may be used according to the present invention is the *Pseudomonas synxantha* PS54A strain deposited under # NCAIM (P) B 001387 according to the Budapest Treaty.

Although we do not wish to restrict the explanation of the antagonist effect according to the present invention to one theory, it can be seen that the unique effect of the biological material according to the invention against the pathogens is on one hand due to that it produces different antibiotics mainly effective against fungi, which are secreted to the extracellular space and on the other hand that it possesses excellent competition characteristics.

The present invention relates to a pesticide composition that comprises a culture of the biological material according to the invention and optionally an excipient.

Based on the above, the excipient according to the present invention is not particularly limited, in condition that it does not decrease the effectiveness of the biological material according to the present invention as an active agent, or a biological and chemical active agent combination, and the applicable excipients include without limitation the following:

a) in case of a liquid formulation e.g. water or an organic solvent (e.g. xilene, methanol, ethylene-glycol or mineral oil), a dispersion stabilizator, a surfactant (e.g. calcium-dodecyl-benzene-sulphonate, polyglycol-ether, etoxylated alkyl-phenol or alkyl-aryl-sulphonates), optionally waxes, b) in case of a granular formulation montmorillonite, bentonite, wood flour, starch, cellulose and a binder, such as e.g. a mineral oil, polyvinyl-alcohol or saccharose, c) and other in itself known, usual additive and/or excipient.

The excipient according to the invention may be selected by the skilled person without undue experimentation.

The dose form according to the present invention is not particularly limited, provided that it is suitable for the application of the biological material according to the invention as active agent, or the composition containing said biological material according to the invention to the protected plant or any part thereof. Such applicable dose forms include without limitation the following: aqueous suspension, suspension concentrate, capsulated concentrate, emulsion forming liquid spray, granule, granule dispersible in water, microgranule, water soluble powder. The dose formulation which may be used according to the invention may be selected by the skilled person without undue experimentation.

Furthermore, the present invention relates to a process for controlling pathogens according to which the biological material or composition according to the invention is applied to a mushroom, preferably to oyster mushrooms and/or champignons. The biological material according to the invention is preferably applied to the surface of the culturing medium, to the fruiting body, to the environment of the protected mushroom, is mixed to the irrigation water of the mushroom and/or sprayed to the protected mushroom, or applied by the combination of any of the above.

The present invention relates to the use of the composition according to the invention for controlling the pests of cultivated mushroom, preferably oyster mushrooms and/or champignons.

The invention furthermore relates to a growth medium for the cultivation of mushrooms, which has been treated with the biological material according to the invention.

In the following, our invention is further detailed through preparation and working examples, referring to the figures listed below, annexed to the description.

EXAMPLES

Isolation of Fluorescent *Pseudomonas* Strains from Oyster Mushroom and/or Champignon Fruiting Bodies

*Pseudomonas*-selective culturing media was used for the isolation. The strains were identified after purification to species level with modern molecular biological methods.

Figure 1:
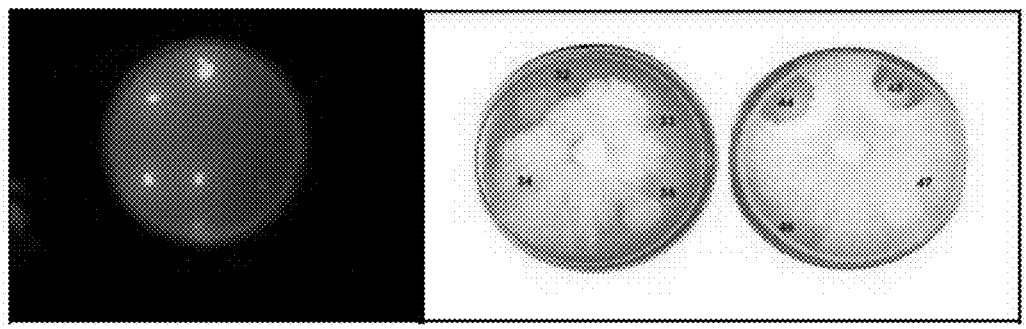
FIG. 1 illustrates the fluorescence of *Pseudomonas* colonies caused by UV radiation on *Pseudomonas* selective S1 culturing medium, furthermore the oyster mushroom inhibition test performed with *Pseudomonas* strains on YEG-culturing medium (0.2% glucose, 0.2% yeast extract, 2% agar).

The isolation of the *Pseudomonas* strains was made on selective S-1 medium. Pulling the mushroom body along the *Pseudomonas* selective (S-1) culturing plate, in case of a strong infection the bacterium colonies appeared within 24 hours. The compost samples were suspended in water, filtered through a plastic filtering plate, then the straw-free liquid leaving the filtering device was concentrated on Millipore filter, and the transfer was made from this (S-1 culturing medium for 1 l: 18 g agar, 10 g saccharose, 10 ml glycerol, 5 g casamino acids, 1 g $NaHCO_3$, 1 g $MgSO_4$, 2.3 g $K_2HPO_4$, 1.2 g SLS (sodium lauryl sarcosinate), 20 mg trimethoprim). Approximately half of the isolates belonged to the *Pseudomonas fluorescens* species group, and accordingly their colonies fluoresced with bluish-white colour in UV light, and a fluorescent area was also seen around the colonies (FIG. 1).

To refine the classification of the isolates, and to reduce the number of the possible groups, further experiments were made, in which the polymorphism of the 16S rDNS gene of the strains was investigated. The coding gene of the RNS part of the smaller sub-element of the 70S ribosome is often used for the investigation of the relationship between the *Pseudomonas* species, for the identification of the species. The restriction endonucleases that form fragments with 200-1500 bp molecular weight during the digestion of the 16S rDNS propagated by PCR reaction may be useful for the evaluation of the polymorphism of the 16S rDNS gene. For the test called in the literature ARDRA test (amplified 16S ribosomal DNA restriction analysis) BsuRI, Hin6I, HinfI, and SacI restriction endonucleases were used in our experiments. The analysis was made on 9 strains from which 8 were classified into different groups on the basis of the preliminary biochemical and cDNS tests. The least groups were achieved after the digestion with the Hin6I enzyme, where altogether three kinds of models were identified. Treating the 16S rDNS fragments with BsuRI enzyme, the number of groups increased to 6, while the highest resolution was experienced with HinRI and SacI restriction enzymes.

The evaluation of the 16S rDNS is sufficient to determine the species specific differences in case of many species, however, we considered this date insufficient. Thus, we started to study the β-subunit of the RNS polymerase (rpoB), which is much less conservative, and sufficiently variable. With the help of the LAPS (5' TGGCCGAGAACCAGT-TCCGCGT 3') (SEQ ID NO: 1) and LAPS27 (5' CGGCT-TCGTCCAGCTTGTTCAG 3') (SEQ ID NO: 2) primers designed for the section, the given region was propagated, and the cleavage patterns were evaluated.

Then, to achieve the molecular determination, a smaller section of the gene was sequenced with rpoB-PSF (5' AGTTCATGGACCAGAACAACC 3') (SEQ ID NO: 3) and rpoB-PTR (5' CCTTGACGGTGAACTCGTTC 3' (SEQ ID NO: 4) and PAR (5' CCTTCACGGTGAATTCGTTC 3') (SEQ ID NO: 5) primers. On the basis of the rpoB gene sequence data a number of strains was isolated from oyster mushrooms, which are presented for demonstration purposes as follows:

*Pseudomonas fluorescens* bv. V 37 pcs.
*Pseudomonas mucidolens* 1 pcs.
*Pseudomonas putida* 4 pcs.
*Pseudomonas entomophila* 1 pcs.
*Pseudomonas fluorescens* bv. I 2 pcs.
*Pseudomonas fluorescens* PfO-1 1 pcs.
*Pseudomonas brenneri* 2 pcs.
*Pseudomonas tolaasii* 2 pcs.
*Pseudomonas synxantha* 1 pcs.
*Pseudomonas syringae* 1 pcs.
*Pseudomonas mandelii* 1 pcs.
*Rhizobium* sp. 3 pcs.
*Ochrobactrum anthropi* 2 pcs.
*Stenotrophomonas* sp. 2 pcs.

The following strains were isolated from champignons:
*Pseudomonas mucidolens* 2 pcs.
*Pseudomonas fluorescens* PfO-1 1 pcs.
*Pseudomonas reptilovora* 3 pcs.
*Pseudomonas fragi* 1 pcs.
*Pseudomonas fluorescens* bv. I 1 pcs.

Antagonisms tests were made with the strains on YEG-culturing medium (0.2% glucose, 0.2% yeast extract, 2% agar) against oyster mushroom and champignon, to select those *P. fluorescent* strains that do not inhibit the growth of the cultivated mushrooms. Among the listed strains, the most suitable was proven to be *Pseudomonas synxantha* PS54 strain isolated by us.

Antagonism and Competition Tests Against *P. tolaasii*

Figure 2:
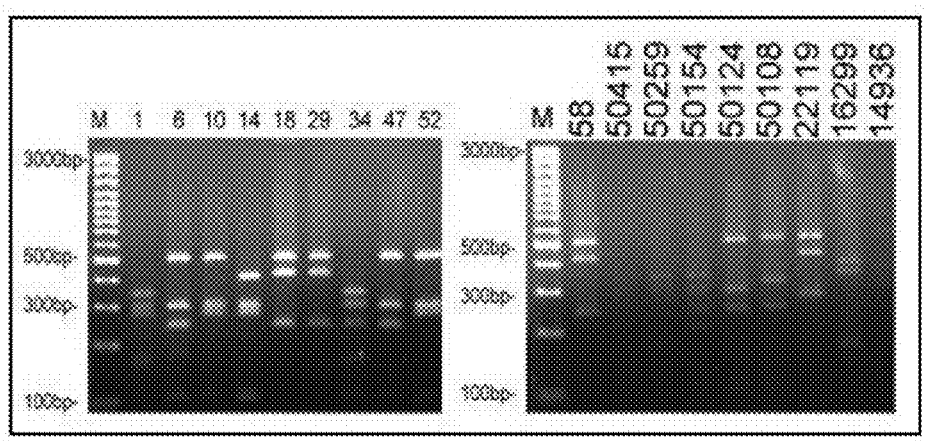
FIG. 2 (comparative) illustrates the rpoB gene RFLP image of the apathogen strains after the comparison with RsaI enzyme; 1: *Pseudomonas fluorescens* bv. V 6: *Pseudomonas fluorescens* bv. V, 10: *Pseudomonas entomophila*, 14: *Pseudomonas putida* bv. A, 18: *Pseudomonas fluorescens* bv. V, 29: *Pseudomonas fluorescens* bv. V, 34: *Pseudomonas brenneri*, 47: *Pseudomonas fluorescens* bv. V, 52: *Pseudomonas fluorescens* bv. V, 58: *Pseudomonas fluorescens* bv. V, 50415: *Pseudomonas fluorescens* bv. IV, 50259: *Pseudomonas cichorii*, 50154: *Pseudomonas fluorescens* bv. V, 50124: *Pseudomonas fluorescens* bv. III, 50108: *Pseudomonas fluorescens* bv. II, 22119: *Pseudomonas constantini*, 16299: *Pseudomonas rhizosphaerae*, 14936: *Pseudomonas poae*, 100 bp Ladder+(M)
Figure 3:
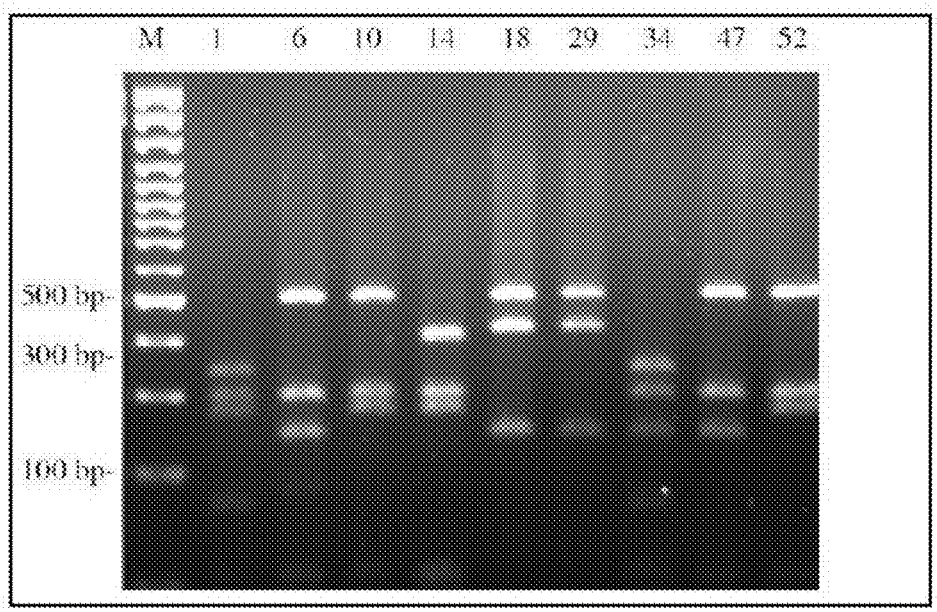
FIG. 3 (comparative) also illustrates the rpoB gene image of the apathogen strains given with RsaI enzyme; 1: *Pseudomonas fluorescens* bv. V 6: *Pseudomonas fluorescens* bv. V, 10: *Pseudomonas entomophila*, 14: *Pseudomonas putida* bv. A, 18: *Pseudomonas fluorescens* bv. V, 29: *Pseudomonas fluorescens* bv. V, 34: *Pseudomonas brenneri*, 47: *Pseudomonas fluorescens* bv. V, 52: *Pseudomonas fluorescens* bv. V, 100 bp Ladder+(M)
Figure 4:
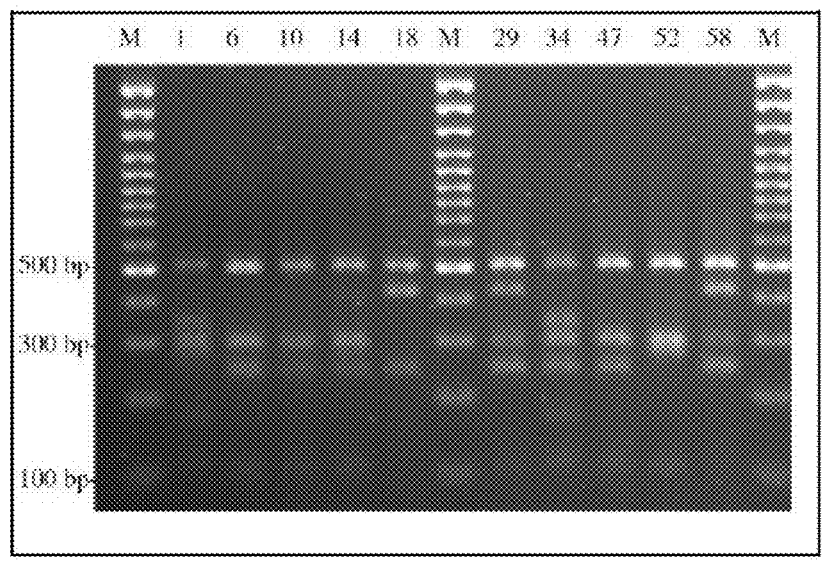
FIG. 4 (comparative) illustrates the images of the combined cultures with RsaI enzyme after the cultivation together with the *Ps. tolaasii* 12213 strain, which show the interactions between the strains. In certain cases the cleavage spectrum characterizing *Ps. tolaasii* completely disappears: *Pseudomonas fluorescens* bv. V 6: *Pseudomonas fluorescens* bv. V, 10: *Pseudomonas entomophila*, 14: *Pseudomonas putida* bv. A, 18: *Pseudomonas fluorescens* bv. V, 29: *Pseudomonas fluorescens* bv. V, 34: *Pseudomonas brenneri*, 47: *Pseudomonas fluorescens* bv. V, 52: *Pseudomonas fluorescens* bv. V, 100 bp Ladder+(M).
Figure 5:
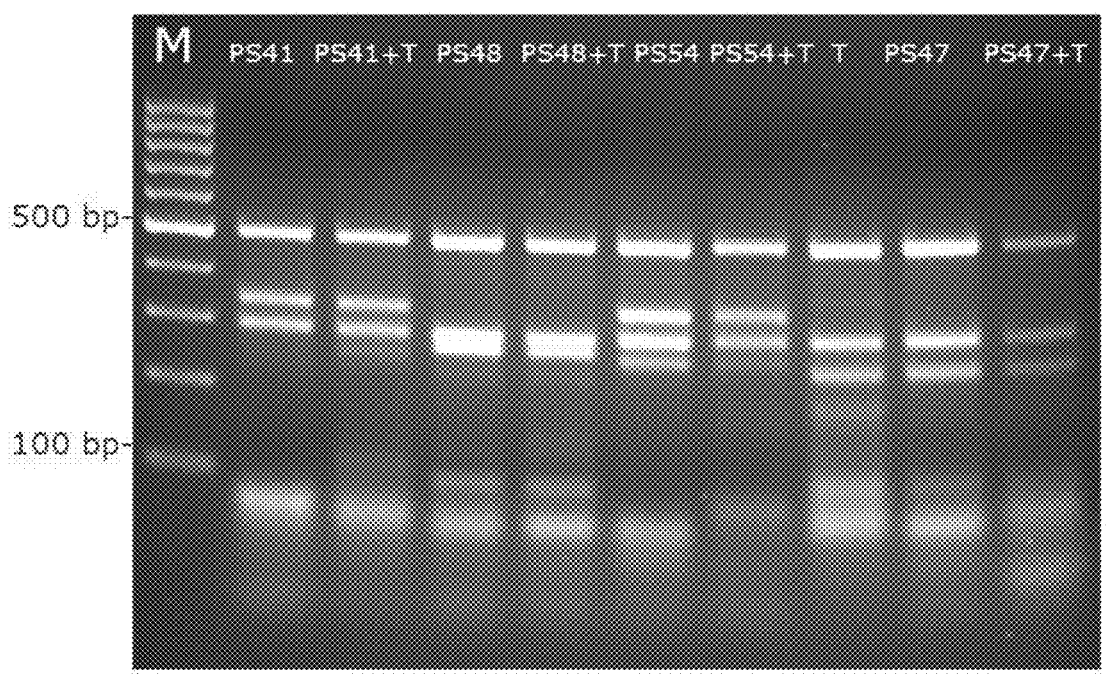
FIG. 5 is the verification of the suppressive effect of *Pseudomonas synxantha* PS54 strain and a few other antagonists against *Pseudomonas Ps. tolaasii* (T) by the RFLP analysis of combined cultures performed with rpoB gene RsaI enzyme.

The antagonizing ability of the apathogen *Pseudomonas* strains isolated from intact fruiting bodies against *P. tolaasii* was evaluated in confrontation tests made on solid culturing medium. Change of the population density of the strains as a function of time was followed using community-ARDRA method in the competition tests performed on culturing media. At the cup-confrontation tests first the potentially useful *Pseudomonas* strains were selected, then we switched to molecular confirmation. This means that after the inoculation of the two strains in the same amount, following a growth overnight, it was evaluated by PCR reaction, which propagates the rpoB sequence. The appearance of the cleavage pattern characterizing the given strain with RsaI and the intensity of the signal were followed (FIG. 4.). To perform this, the cleavage patterns of the *Pseudomonas tolaasii* and the apathogen, selected strains demonstrated alone must be known (FIGS. 2-3 and 5.).

The Effectiveness of the Antagonist *Pseudomonas* Strains in Champignon and Oyster Mushroom Cultures in the Environment of an in vivo Producing Plant In the large-scale technology of the oyster mushroom production the mushroom producers use plastic mushroom production sacks or blocks, from which the bunches of the fruiting bodies appear at the perforations. On the basis of the tests of the treated substrate samples it become known that the pathogen bacteria causing the bacterial maculation cannot be found in the inner part of the culturing medium, thus admixing of the antagonist bacterium to the culturing medium was not necessary. However, the earlier tests demonstrated that the pathogens may occasionally pullulate in the condense water collected on the surface of the substrate (the pH of which is slightly alkaline as opposed to the substrate), therefore knowing the encroaching points of the large-scale technology, we decided to apply surface treatments.

Both with oyster mushroom and with champignon the bacterium strains with the best antagonist effect were selected from the tested ones, and the further experiments were made with these selected strains. With the experiments we intended to test the antagonist activity of the promising bacterium candidates within a normal large-scale production environment.

Experiments with Oyster Mushrooms

The selected best antagonist strains (PS29, PS46, PS54 és PS2) were tested in a pilot-plant environment. In the present case the pilot-plant experiment meant the following: a mushroom cultivation medium produced in a large-scale process was used (25 kg/block), and the experiments were made within a large-scale environment; the only manual action was the application of the active composition. The experiments were made with ten parallel, water control and complete control treatments, using 30 tons of production substrate (1 plastic tunnel production unit). The number of experiments: 4 (see: Table 1).

Treatment: The perforations of the cultivation medium blocks were sprayed with a $10^6$ cell/ml concentration suspension of the antagonist bacterium strains immediately after the completion of the mycelium growth in the period of the appearance of the primordiums. 1 ml suspension was applied to each perforation. The treatment was repeated two days after. The effect of the treatment on the development of the fruiting body, the yield and the appearance of the disease was evaluated.

Discoveries, Results

The treatment had a definitely negative effect on the primordiums, which may not have been the effect of the antagonist bacteria, rather that of the sprinkling water, as the yield of the control blocks was 17.4% better (17.4 kb mushroom/100 kg substrate), while that of the antagonist treated blocks was 12.55-16%, and that of the water treated ones was 11.82%. (see: Table 1). Therefore the method for the treatment needed to be redesigned to decrease the yield reducing risk accompanying the treatment.

TABLE 1

The yield of the different treatments (kg mushroom/100 kg starting material, expressed in percentage)

| Strain | I. | II. | III. | IV. | Average | Deviation |
|---|---|---|---|---|---|---|
| PS29 | 8 | 14 | 14.6 | 13.6 | 12.55 | 2.650943 |
| PS46 | 7 | 17 | 15.2 | 13.1 | 13.075 | 4.352298 |
| PS54 | 16 | 16 | — | — | 16 | 0 |
| PS2 | — | — | 17.4 | 10.9 | 14.15 | 4.596194 |
| Water | 14 | 10 | 14.6 | 8.7 | 11.825 | 2.917048 |
| Control | 17 | 17 | 18.2 | 15 | 17.4 | 0.69282 |

Comparing the different antagonist strains on the basis of their effect on the yield, the best are PS54 and PS2 strains, while the effects of PS29 and PS46 strains produced yields similar to that of the treatments with water

TABLE 2

The effect of the different treatments on the quality of the mushroom (the proportion of the healthy fruiting blocks are expressed in percentage)

| Strain | I. | II. | III. | Average |
|---|---|---|---|---|
| PS2 | — | — | 70% | 70% |
| PS29 | 60% | 60% | 50% | 57% |
| PS47 | 60% | 90% | 60% | 70% |
| PS54 | 80% | 80% | — | 80% |
| Control | 40% | 70% | 60% | 57% |

Testing the in vivo efficacy of the treatments, as it is prohibited to perform experiments with provoked infections in large-scale circumstances, the level of infection of the treated stock was compared to that of the control block (see: Table 2). It can be seen from the table that PS54, PS47 and PS2 strains exhibited antagonizing effect as compared to the control against the pathogens.

On the basis of the experiments in the oyster mushroom production system, among the tested strains, PS54 proved to have the best effect both in the yield and in the effectiveness against the disease, therefore it can be stated that this strain is worth using as a pest control bacterium against bacterial maculation.

In case of the champignon species, our preliminary studies demonstrated that the PS54 *Pseudomonas synxantha* strain can ensure the most effective protection by admixing to the cultivation substrate against the *Pseudomonas* causing rotting disease. 20-30% reduction of the damages may be achieved in both systems by using the bacterium strain. On the basis of the results, the subject of the claims appended to the present description is the *Pseudomonas synxantha* PS54 strain ensuring the best effect.

INDUSTRIAL APPLICABILITY OF THE INVENTION

It is a benefit of the present invention that the isolated *Pseudomonas synxantha* PS54 strain induces a strong antagonist effect against pathogens of the oyster mushroom and champignon, especially against *Pseudomonas tolaasii* and *Pseudomonas agarici* and thus it increases the proportion of the intact fruiting bodies in the mushroom production.

What is claimed is:

1. A process for controlling mushroom pathogen *Pseudomonas tolaasii*, said process comprising contacting cultivated mushrooms with an effective concentration of *Pseudomonas synxantha* PS54 bacteria strain deposited under number NCAIM (P) B 001387 according to the Budapest Treaty, or a composition containing the strain and an excipient to antagonize *Pseudomonas tolaasii*, said process further comprising isolating, purifying and concentrating the strain before the contacting.

2. The process according to claim 1, wherein said contacting comprises:
   a) contacting a surface of the culturing medium of the mushroom with the strain or the composition,
   b) contacting a fruiting body of the mushroom with the strain or the composition,
   c) contacting an environment of the mushroom with the strain or the composition, wherein the environment is a production sack or block,
   d) mixing the strain or the composition with irrigation water for the mushroom and contacting the mushroom with the resultant mixed irrigation water,
   e) mixing the strain or the composition with culturing medium for the mushroom and contacting the mushroom with the resultant mixed culturing medium,
   f) spraying the mushroom with the strain or the composition;
   and/or applying any combination of any of a)-f).

3. The process of claim 1, wherein the mushrooms are oyster mushrooms and/or champignon.

4. The process of claim 1, wherein the composition is in an aqueous suspension, suspension concentrate, capsulated concentrate, emulsion forming liquid spray, granule, granule dispersible in water, microgranule or water soluble powder dose formulation.

5. The process of claim 1, wherein the strain is in a concentration of $10^6$ cell/ml.

* * * * *